US008674304B2

(12) United States Patent
Zhang et al.

(10) Patent No.: US 8,674,304 B2
(45) Date of Patent: Mar. 18, 2014

(54) PLASMA DIAGNOSTIC METHOD USING TERAHERTZ-WAVE-ENHANCED FLUORESCENCE

(75) Inventors: Xi-Cheng Zhang, Melrose, NY (US); Jingle Liu, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 99 days.

(21) Appl. No.: 13/097,866

(22) Filed: Apr. 29, 2011

(65) Prior Publication Data

US 2012/0193535 A1   Aug. 2, 2012

Related U.S. Application Data

(60) Provisional application No. 61/343,480, filed on Apr. 29, 2010.

(51) Int. Cl.
*G01J 5/02* (2006.01)
(52) U.S. Cl.
USPC .......................................... 250/341.1
(58) Field of Classification Search
USPC ........................................ 250/341.1–341.8
See application file for complete search history.

(56) References Cited

U.S. PATENT DOCUMENTS

| 7,550,734 | B1 * | 6/2009 | Lee et al. ................. 250/370.12 |
| 7,659,513 | B2 * | 2/2010 | Gorrell et al. .............. 250/341.1 |
| 2007/0167832 | A1 * | 7/2007 | Yaniv et al. .................. 600/475 |
| 2008/0245964 | A1 * | 10/2008 | Miles et al. ................... 250/288 |
| 2008/0265165 | A1 * | 10/2008 | Yeh et al. .................... 250/341.1 |
| 2009/0066948 | A1 * | 3/2009 | Karpowicz et al. ........... 356/326 |
| 2010/0271056 | A1 * | 10/2010 | Irisawa et al. ................. 324/750 |
| 2010/0277718 | A1 * | 11/2010 | Zhang et al. .................... 356/51 |
| 2011/0057103 | A1 * | 3/2011 | Nishina et al. ............. 250/338.1 |
| 2011/0090500 | A1 * | 4/2011 | Hu et al. ....................... 356/337 |
| 2011/0204235 | A1 * | 8/2011 | Majewski et al. ........ 250/339.08 |

OTHER PUBLICATIONS

Author : Norman Laman et al., Title: Intense and Broadband THz Source using Laser-Induced Gas Plasma, Date: Aug. 27, 2009, Publisher: Zomega Terahertz Corporation.*
Author : Peter H. Siegel et al., TitleTerahertz Heterodyne Imaging Part II: Instruments, Date: May 2006, Publisher: International Journal of Infrared and Millimeter Waves, vol. 27.*

* cited by examiner

*Primary Examiner* — David Porta
*Assistant Examiner* — Taeho Jo
(74) *Attorney, Agent, or Firm* — Heslin Rothenberg Farley & Mesiti P.C.

(57) ABSTRACT

Methods and systems for characterizing a plasma with radiation, particularly, terahertz (THz) radiation, are disclosed. The disclosed method of characterizing a plasma includes directing THz radiation into the plasma; and detecting an emission due to interaction of the THz radiation with the plasma to characterize the plasma. A disclosed plasma characterizing device includes a means for directing THz radiation into a plasma; and a detector adapted to detect an emission emitted by the plasma due to interaction of the THz radiation with the plasma to characterize the plasma. A plasma characterizing system is also disclosed. The emission detected may be a fluorescence, a variation in fluorescence and/or an acoustic emission.

20 Claims, 6 Drawing Sheets

PLASMA DIAGNOSTIC METHOD USING TERAHERTZ-WAVE-ENHANCED FLUORESCENCE

CROSS REFERENCE TO RELATED APPLICATIONS

This application claims priority under 35 U.S.C. §119 to U.S. provisional application No. 61/343,480 filed Apr. 29, 2010, which is herein incorporated by reference in its entirety.

This application is related to pending U.S. application Ser. No. 13/095,267 filed on Apr. 27, 2011, the disclosure of which is included by reference herein in its entirety.

This application is also related to pending PCT Application PCT/US11/34466 filed on Apr. 29, 2011, the disclosure of which is included by reference herein in its entirety.

STATE AND FEDERAL FUNDED RESEARCH

The invention described herein was made with U.S. Government support under contract Number 2008-ST-061-ED0001 awarded by the Department of Homeland Security (DHS); under Contract Number NSF0923353 awarded by the National Science Foundation (NSF); and under Contract Number HDTRA11-09-1-0040 awarded by the Defense Threat Reduction Agency (DTRA). The U.S. Government has certain rights to this invention.

BACKGROUND OF THE INVENTION

1. Field of the Invention

The present invention generally relates to methods and systems for investigating plasmas. In particular, aspects of the invention relate to detecting changes in fluorescence of a plasma due to terahertz radiation to analyze plasmas.

2. Description of Related Art

In the field of plasma Physics, a "plasma" is a state of matter similar to gas in which a certain portion of the particles are ionized. Various plasma diagnostic methods have been employed in experimental plasma physics to characterize the physical properties of plasma, such as density, temperature and collision frequency. Langmuir probe, plasma spectroscopy, microwave, optical interferometry and Thomson scattering are commonly used to measure plasma density.

One type of plasma typically encountered is laser-pulse induced plasma. Laser-pulse-induced plasma is transient in nature with a fast temporal evolution of parameters. A detailed understanding of the fast dynamics of laser-induced plasma is of great importance to potential applications in plasma chemistry, high harmonics generation, wakefield acceleration, and self-guided filament propagation. The plasma inside the laser filaments has been characterized by several investigations using the methods described above. For example, the electric conductivity measurement provides direct density information of the plasma channel with a temporal resolution of nanoseconds. Also, optical interferometric methods are capable of resolving the plasma dynamics with sub-picosecond resolution.

However, a need exists to provide tools for analysis of plasmas, for example, the transient nature plasmas, in particular, to analyze laser-pulse-induced plasmas.

SUMMARY OF THE INVENTION

A plasma diagnostic method based on terahertz (THz) time-domain spectroscopy, providing high temporal resolution and THz bandwidth coverage, is introduced.

One embodiment of the invention is a method of characterizing a plasma, including: directing THz radiation into the plasma; and detecting an emission due to interaction of the THz radiation with the plasma to characterize the plasma. In one aspect of the method, the emission comprises at least one of a fluorescence emission and an acoustic emission. In another aspect of the invention, the method also includes determining a characteristic of the plasma by analyzing the detected emission. In another aspect of the invention, the characteristic of the plasma detected in the method includes at least one of plasma density, plasma scattering frequency, plasma relaxation time, and plasma electron density. In another aspect of the invention, the method step of detecting florescence includes detecting variation in the fluorescence. In still another aspect of the invention, the method also includes comparing the variation in florescence to a variation of florescence of known plasmas. In another aspect of the invention, the method also includes fitting the detected variation in florescence to a known equation to characterize the plasma. In still another aspect of the invention, the method also includes comparing the detected emission with emission of a known plasma. In another aspect of the invention, THz radiation of the method comprises a pulse energy; and the method also includes varying the pulse energy of the THz radiation. In another aspect of the invention, the method also includes repeating the steps of directing the THz radiation into the plasma and detecting the variation in emission.

Another embodiment of the invention is a plasma characterizing device including: a means for directing THz radiation into a plasma; and a detector adapted to detect emission emitted by the plasma due to interaction of the THz radiation with the plasma to characterize the plasma. In another aspect of the invention, the plasma characterizing device also includes a means for directing a laser into a gas to create the plasma. According to another aspect of the invention, the plasma characterizing device, the THz radiation is a pulsed beam. In another aspect of the invention, the detector of the plasma characterizing device includes: a means for collecting emission; and a means for measuring emission. In another aspect of the invention, the detector of the plasma characterizing device also includes a filter.

Another embodiment of the invention is a plasma characterizing system, including: a gas cell, the gas cell including a gas inlet, configured to allow a gas to enter the gas cell; the plasma characterizing system also including a laser configured to be directed on the gas within the gas cell, and to excite at least some of the gas to form a plasma; a source of THz radiation configured to direct the THz radiation into the plasma; and an emission detector positioned to collect the florescence of the plasma. According to another aspect of the invention, the plasma characterizing device also includes one or more interference filters. According to another aspect of the invention, the plasma characterizing device also has a collecting lens positioned between the plasma and the fluorescence detector. In still another aspect of the invention, the plasma characterizing, the THz radiation comprises a Terahertz pulse. According to another aspect of the invention, the plasma characterizing device also includes a means for varying an energy of the THz pulse. In yet another aspect of the invention, the plasma characterizing device also includes a means for varying a time delay between a laser pulse and the THz pulse.

These and other features and advantages of this invention will become apparent from the following detailed description of various aspects of the invention taken in conjunction with the following drawings.

DETAILED DESCRIPTION OF THE DRAWINGS

A method of characterizing a plasma using a Terahertz-wave-enhanced fluorescence emission from excited gas molecules/ions is described herein. The dynamic properties of nitrogen/helium gas plasma at different densities and laser excitation intensities ($10^{13} \sim 10^{14}$ W/cm$^2$) have been systematically investigated, and can be used to characterize a plasma. The time-dependent enhanced fluorescence is used to deduce one or more characteristic of a plasma, for example, electron relaxation time and plasma density. The systems and methods can provide picosecond temporal resolution and omni-directional optical signal collection which can circumvent the limitation of the signal collection in the forward direction.

The inventors investigated the interaction between single-cycle THz pulses and laser-induced gas plasma through observing the THz-wave-enhanced fluorescence emission from the plasma. It has been found that certain characteristics of a plasma can be determined from the emitted fluorescence. These characteristics can be compared, for example, to the characteristics of an unknown plasma to characterize, for example, identify, the plasma. The characteristics of other plasmas may be determined for comparison to unknown plasmas. The time-dependent, enhanced fluorescence is attributed to the THz-wave-induced electron heating, electron impact ionization of high-lying trapped states and subsequent increased population of fluorescing upper states. The time-dependent, enhanced fluorescence has the form:

$$\Delta I_{FL}(\tau, t_d) \propto n_e(\beta_{ei}, t_d) \sum_{i=1}^{\infty} \Delta \vec{v}_i^2(\tau, t_d),$$

where $n_e$ is the electron density as a function of electron-ion recombination rate $\beta_{ei}$, and the time delay between laser pulse and the peak of the THz pulse, $t_d$. $\tau$ is the average electron relaxation time. H $$\Delta \vec{v}_i^2(\tau, t_d) = -\int_{t_d+(i-1)\tau}^{t_d+i\tau} e\vec{E}_{THz}(t) dt/m$$

is the change of electron velocity in the THz field $\vec{E}_{THz}$ in between two neighboring collisions at time $t_{i-1}=t_d+(i-1)\tau$ and $t_i=t_d+i\tau$, respectively. $\tau$ and temporal evolution of $n_e$ can be determined from the measured time-dependent, enhanced fluorescence.

Figure 1:
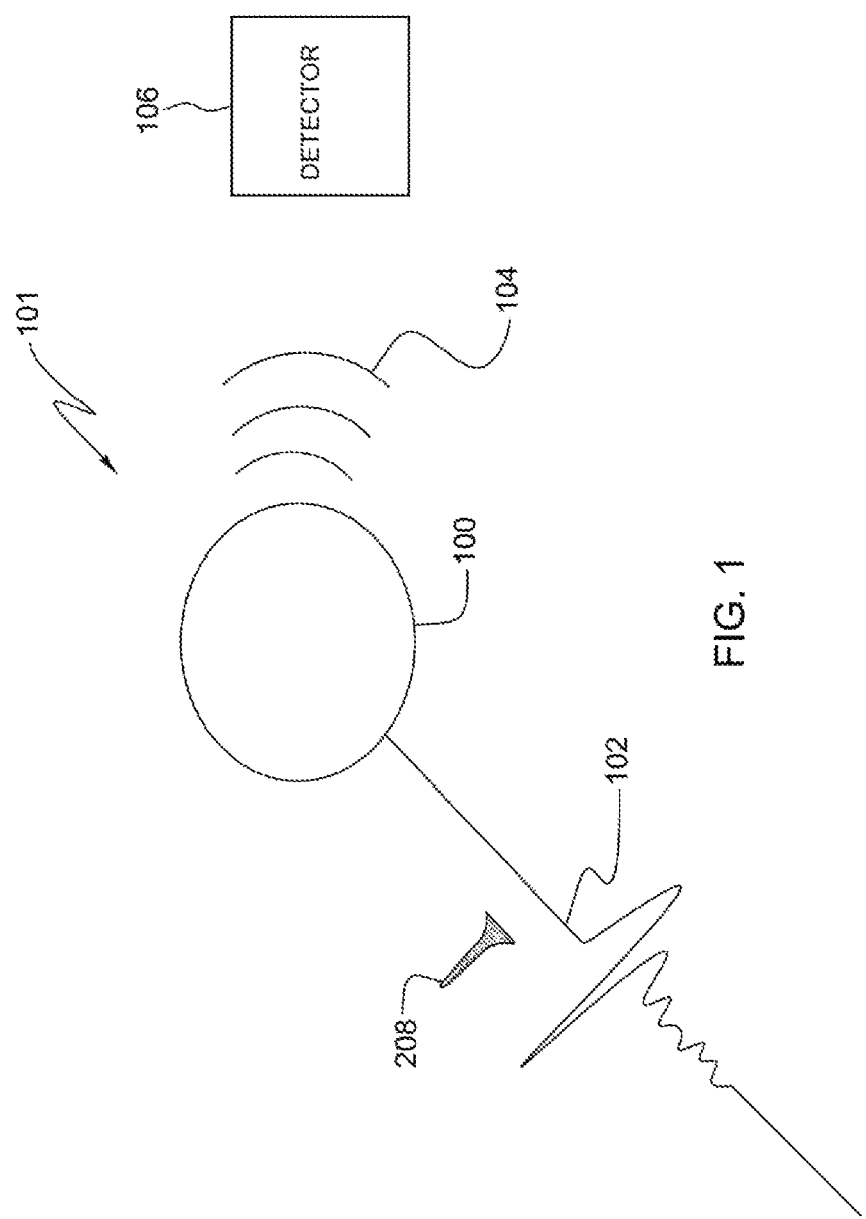
FIG. 1 is a schematic illustration of a device and a system for characterizing a plasma according to one aspect of the invention.

FIG. 1 is a schematic illustration of a system and method 101 for characterizing a plasma according to one aspect of the invention. FIG. 1 shows a plasma 100 created by any known means of creating a plasma, for example, laser excitation, and Terahertz radiation wave 102 directed into the plasma 100. The Terahertz radiation 102 may be a pulse as shown in FIG. 1 adapted to produce at least some fluorescence radiation or fluorescence 104 when interacted with plasma 100. The fluorescence 104 from the plasma 100 due to the interaction with THz radiation may be directed in any direction, for example, it may be omni-directional. According to aspects of the invention, fluorescence 104 is detected by a detector 106 and the detected fluorescence can then be used to characterize the plasma 100. Though the radiation wave 102 shown in FIG. 1, is shown as a THz wave, in some aspects of the invention, the radiation wave 102 may be any electromagnetic radiation, for example, microwaves, infrared waves, visible light, ultraviolet (UV) light extreme ultraviolet (EUV) light, x-rays, gamma rays, and radio waves.

According to aspects of the invention, one or more characteristics of plasma 100 may be detected based upon one or more emissions from plasma 100 due to interaction of plasma 100 with radiation wave 102. In one aspect, for example, as described in co-pending application U.S. application Ser. No. 13/095,267 (include by reference herein), the emission 104 from plasma 100 may comprise fluorescence or variation in fluorescence, such as UV fluorescence, due to interaction of radiation wave 102 with plasma 100. In another aspect, as described in co-pending application PCT Application PCT/US11/34466 (include by reference herein), the emission 104 from plasma 100 may comprise an acoustic signal or a variation in an acoustic signal due to interaction of radiation wave 102 with plasma 100. In one aspect of the invention, the emission may be both acoustic and fluorescence.

Figure 2:
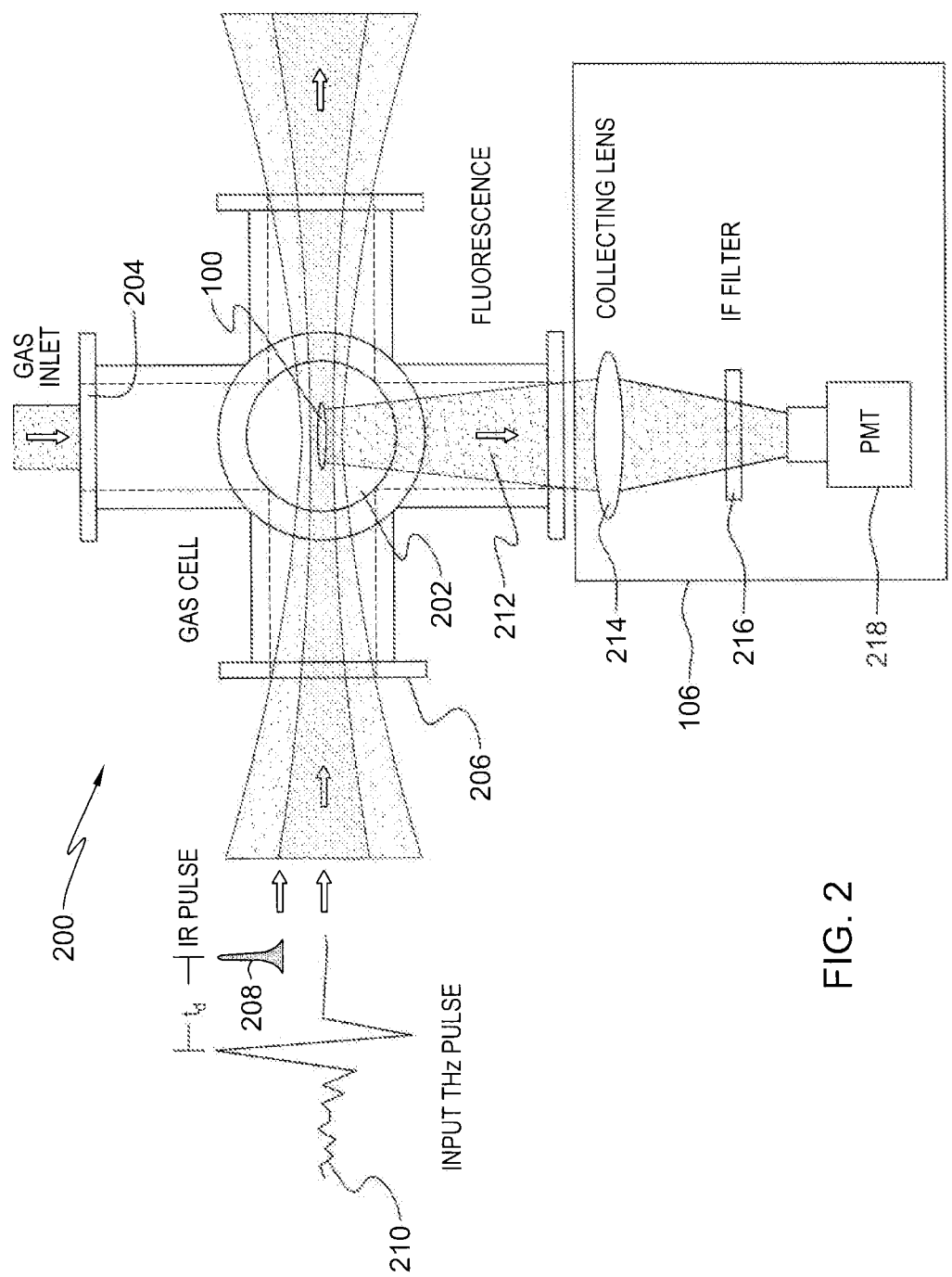
FIG. 2 is a schematic illustration of a plasma characterizing system according to one aspect of the invention.

FIG. 2 is a schematic illustration of a plasma characterizing system 200, according to one aspect of the invention. FIG. 2 shows an example of an experimental plasma characterizing system 200 that may be used to detect fluorescence due to THz radiation 210. For example purposes, a gas cell 202 is shown. The gas cell 202 is capable of retaining a gas, for example air or nitrogen, at a specified pressure and concentration. The gas cell 202 includes a gas inlet 204. Gas inlet 204 may allow gas to fill the gas cell 202 to a desired pressure and concentration. A radiation inlet 206 is provided through which radiation of various types may be introduced. As shown in FIG. 2, a plasma 100, for example, as shown in FIG. 1, may be formed within gas cell 202 by radiation introduced through the radiation inlet 206. For example purposes, FIG. 2 shows plasma 100 produced by an optic beam or pulse 208, which may be, for example a femtosecond laser pulse. According to aspects of the invention, terahertz radiation 210 may be focused on plasma 100. The Terahertz pulse 210 interacts with plasma 100 to produce a fluorescence 212, which propagates in substantially every direction. As shown in FIG. 2, a detector 106 may be placed in substantially any direction to detect fluorescence 212 or a change in fluorescence 212. Under illumination by an optical beam, for example, an intense femtosecond [fs] laser pulse, the molecules in at least a portion of the volume of gas are excited and then ionized by releasing one or more free electrons through multi-photon ionization or tunneling ionization. It is conjectured that after rejection from the atoms or molecules during the leading part of the laser pulse, the electrons are accelerated by the rest of the laser pulse and drift away from their parent ions. In this intense laser field excitation, the electron temperature is usually much higher than the temperature of the neutral particles, for example, mostly molecules in air and ions, having masses that are generally thousands of times larger than electron mass. Before the electron-ion recombination, these "hot" electrons collide with the neighboring "cold" molecules and transfer some portion of their kinetic energy to the molecules through the inelastic electron-molecule collision in the following nanoseconds to produce fluorescence 212, for example, UV fluorescence.

System 200 typically includes a detector 106 adapted to detect fluorescence 212. Detector 106 may be comprised of a collecting lens 214, an interference filer 216, and a photo-multiplier tube 218, though other types of detectors and detector components may be used.

For example purposes, a femtosecond laser pulse 208 may be created by a laser with a convex lens having about 100 mm effective focal length. The laser pulse 208 may have a wavelength of about 800 nm and a pulse duration of about 80 femtoseconds. The pulse energy of the laser pulse 208 may vary from 60 µJ to 150 µJ. The optical intensity at the focus of the laser pulse 208 is in the range of $10^{13}$~$10^{14}$ W/cm². Alternative known laser pulse energies, durations, wavelengths and lenses may be used to create the plasma. Still other known means of creating a plasma may be used to create the plasma.

The THz radiation 210 may be a pulsed wave, generated by a known means of producing pulsed terahertz waves. For example purposes, a single-cycle THz pulse with pulse width of 1 picosecond (ps), a center frequency of 1 THz, and a peak field of 100 kV/cm can be focused on the plasma 100. In one embodiment, the THz pulse is directed collinearly with the laser pulse. However, in alternative embodiments, the THz pulse may be directed on the plasma from substantially any direction. The experimental set up may include, for example purposes, 1 mm thick quartz plates that allow for the transmission of laser and THz radiation.

Still referring to FIG. 2, the time-domain waveform of the THz pulse may be measured by conventional electro-optical sampling for comparison to the detection according to aspects of the invention. The fluorescence 212 emission of the gas plasma 100 may be collected by the collecting lens 214, and passed through an interference filter 216. The collecting lens 214 may be a convex lens. The photo-multiplier tube 218 measures the fluorescence 212 emission. Other known means of detecting fluorescence or changes or variations in fluorescence may be used in place of the detector 106 described here.

As also shown in FIG. 2, in one aspect, there may be a temporal relationship between laser pulse 208 and Terahertz pulse 210, for example, the timing of impact of laser pulse 208 upon a portion of the volume of gas and the impact of Terahertz wave 210 on the portion of the volume of gas may be separated by a time delay $t_d$. Time delay $t_d$ may be positive, negative, or substantially zero, and, according to an aspect of the invention, may be variable or controllable. According to aspects of the invention, a negative time delay, $t_d$, represents a condition in which the plasma generating laser pulse 208 leads the Terahertz pulse 210, that is, laser pulse 208 impacts or is present within the portion of the volume of gas before the Terahertz pulse 210. The inventors have found that when the time delay $t_d$ is negative (that is, laser pulse 208 precedes the Terahertz pulse 210), the fluorescence 212 is observed to be enhanced by the radiation wave field, for example, the THz radiation field.

Figure 3:
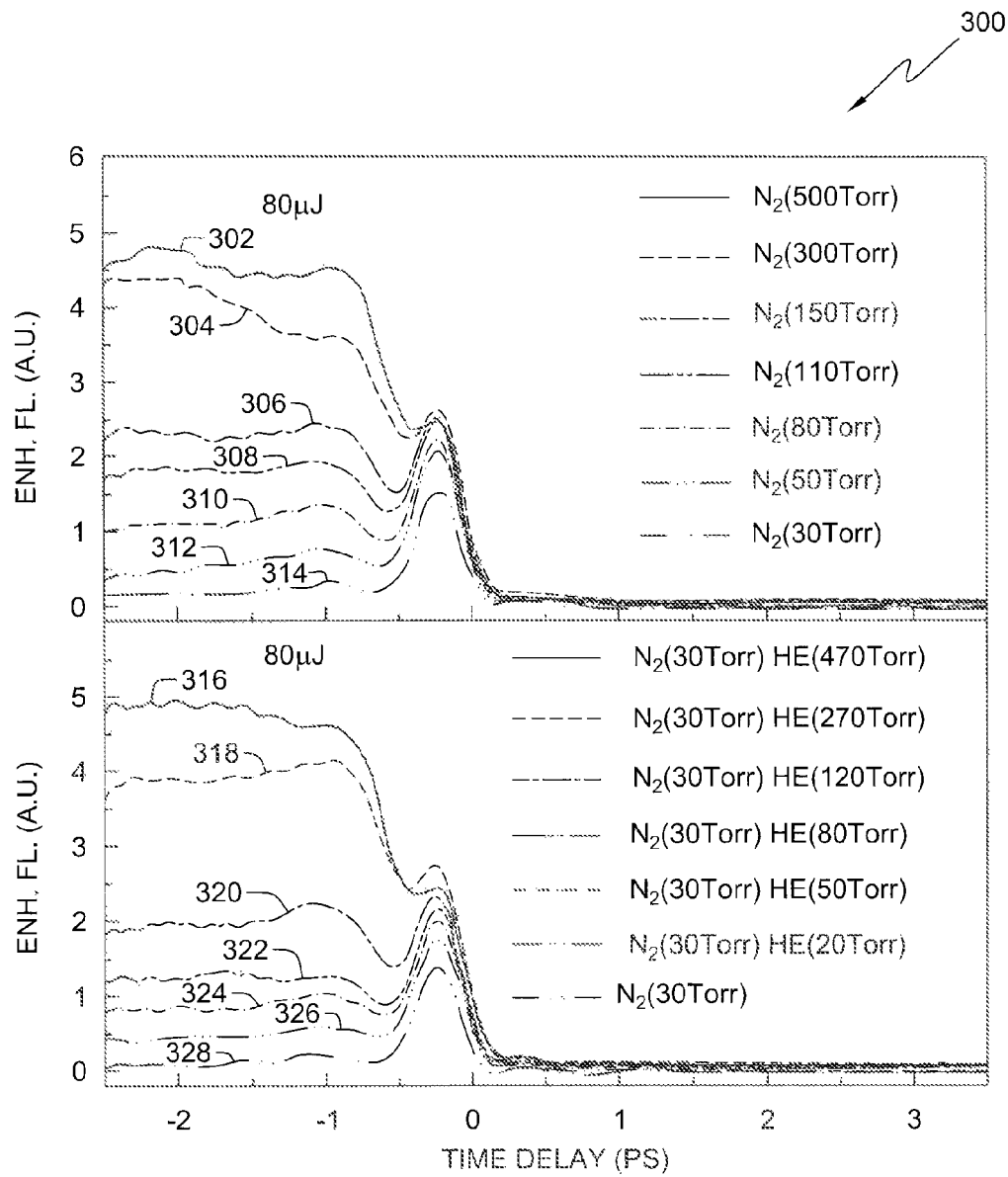
FIG. 3 is a graphical representation of fluorescence detected for nitrogen gas and nitrogen-helium mix at varying pressures according to one aspect of the invention.

FIG. 3 is a graphical representation 300 of enhanced or variation in fluorescence detected for nitrogen gas and nitrogen-helium mix at varying pressures, according to one aspect of the invention. FIG. 3 illustrates the curves of the time-dependent, enhanced fluorescence at different pressures in pure nitrogen gas and in nitrogen-helium gas. Understanding intrinsic properties of nitrogen gas, constituting 78% of the earth's atmosphere by volume, is essential to many atmospheric laser applications. Laser-induced nitrogen plasmas were investigated by the inventors. Curves 302-314 represent the time-dependent fluorescence of pure nitrogen at the specific pressure identified in FIG. 3. For curves 302-314, a narrow-band interference filter with center transmission wavelength of 357 nanometers (nm) and full-width-half-magnitude of 10 nm was used to transmit the strongest line in the second positive band system of nitrogen molecules. As shown in FIG. 3, enhanced fluorescence increases with pressure according to aspects of the invention. Additional results were obtained by adding Helium as a buffer gas. Curves 316-328 represent the time-dependent fluorescence of Nitrogen-Helium mixtures at the spectral pressures identified. For the THz intensities shown in FIG. 3, the helium gas remains almost non-ionized because the ionization potential 24.6 eV is too high for the ionization to be appreciable. However, the addition of helium atoms changes the electron collision frequency. The changing electron collision frequency is best illustrated by the curves of the Nitrogen-Helium gas mixtures in FIG. 3.

The pressure dependent behaviors illustrated in FIG. 3 indicate that the collision frequency is dependent on the total particle density. The average relaxation time of a free electron can be estimated from the scattering cross section, the average electron velocity and the total scatterer density. For example, when a 80 µJ Terahertz pulse is used, the ionization degree is very low, and the total scatterer density is dominated by the neutral particle density, which is proportion to pressure. The scattering cross sections of helium and nitrogen are in the same order of magnitude and the initial electron velocity is determined by the optical intensity, therefore the electron relaxation time is largely determined by the total scatterer density. Under high pressure, the time-dependent enhanced fluorescence follows a generally double step path, as shown by curves 302, 304, 316 and 318. When the gas is under a lower pressure, the time-dependent enhanced fluorescence is zero for a large negative time delay, as shown by curves 312 and 328. The average electron relaxation time was determined from the measured time-dependent enhanced fluorescence using a room mean square minimization algorithm.

Figure 4:
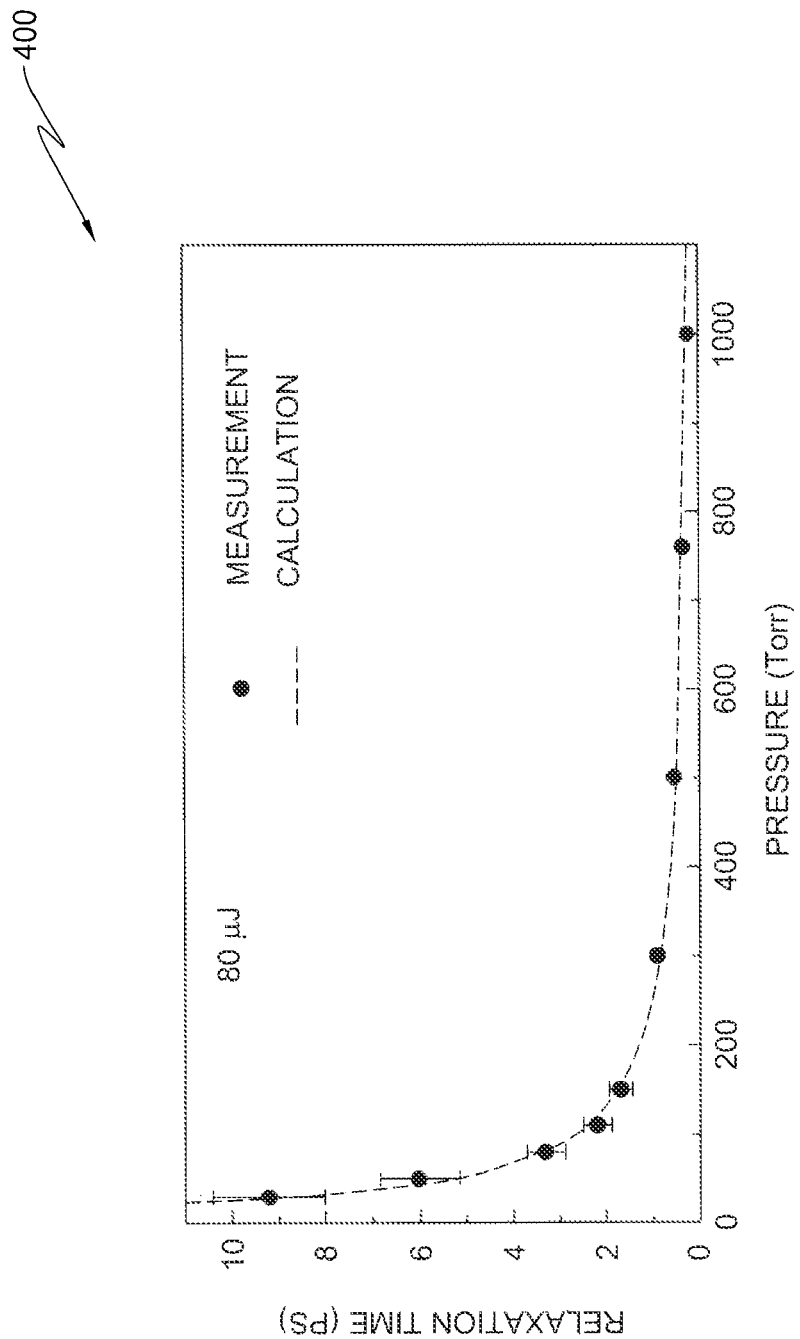
FIG. 4 is a graphical representation of a comparison of measured and calculated relaxation time according to one aspect of the invention.

FIG. 4 is a graphical representation 400 of a comparison of measured and calculated relaxation time, according to one aspect of the invention. FIG. 4 shows the relaxation time of the electrons in relation to the pressure of the gas. As known in the art, relaxation time is defined as the amount of time required for the excited molecules to return to a state of rest, in this case, the amount of time required for the plasma to return to the gas state. Both the calculated relaxation time and measured relaxation time are shown. As expected, the relaxation time decreased as the pressure increased.

Figure 5:
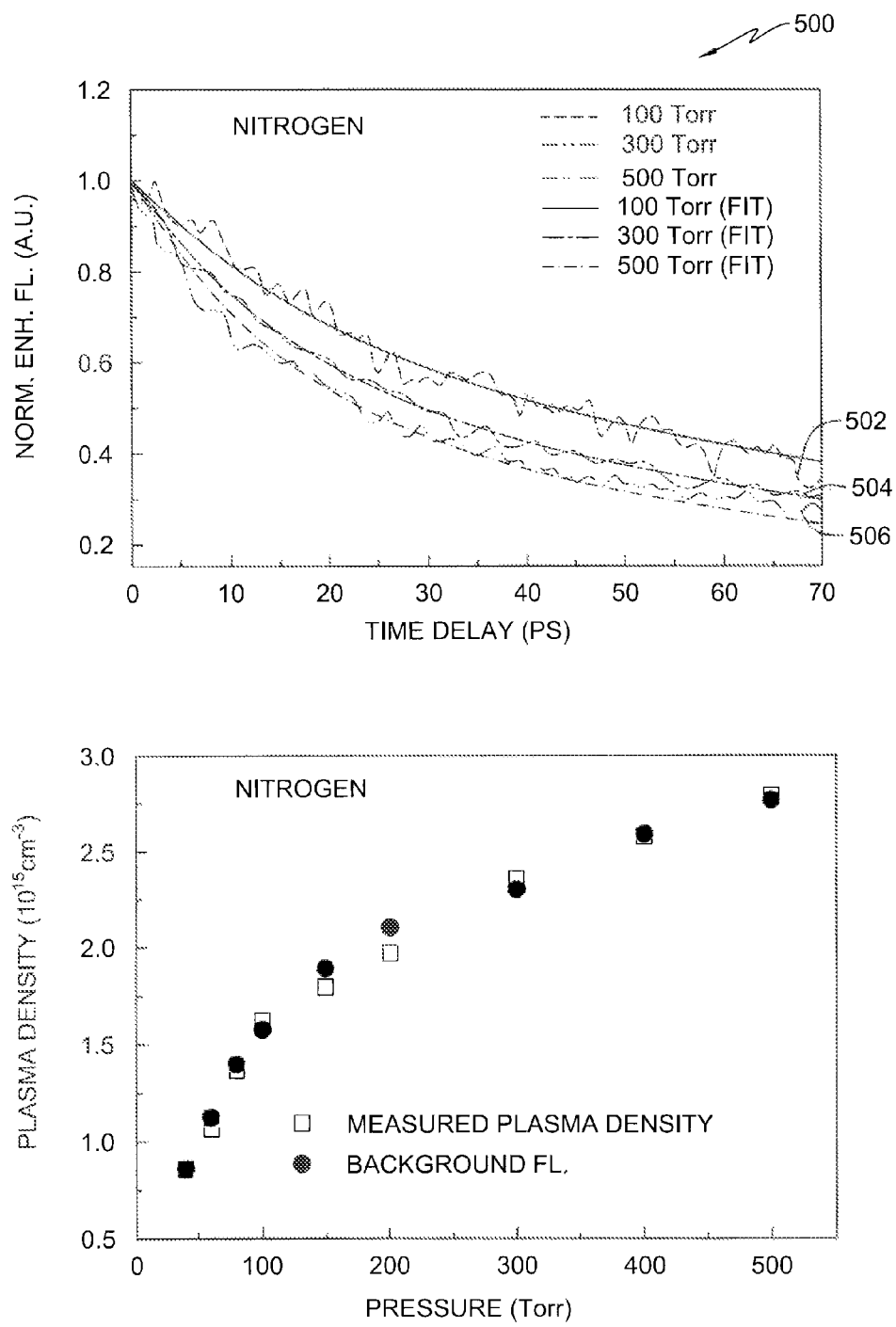
FIG. 5 is a graphical representation of measured fluorescence and best fit of fluorescence at varying pressures, and a graphical representation of a comparison on plasma density to background fluorescence for varying pressures according to one aspect of the invention.

FIG. 5 is a graphical representation 500 of measured enhanced or variation in fluorescence and best fit of enhanced fluorescence at varying pressures, and a graphical representation comparing plasma density to background fluorescence for varying pressures, according to one aspect of the invention. FIG. 5 shows the measured enhanced florescence and a fitted curve of the measured enhanced fluorescence as the time delay, $t_d$ between the Terahertz radiation and the femtosecond laser pulse. As the time delay increases, the enhanced fluorescence decreases. The fit line is used as an approximation of the electron density equation. As an estimation, different rates of decay occur under differing pressures. FIG. 5 also shows the plasma density relative to the pressure of the gas. Curve 502 shows the time-dependent enhanced fluorescence at 100 torr. Curve 504 shows the time-dependent enhanced fluorescence at 300 torr. Curve 504 shows the time-dependent enhanced fluorescence at 500 torr.

Figure 6:
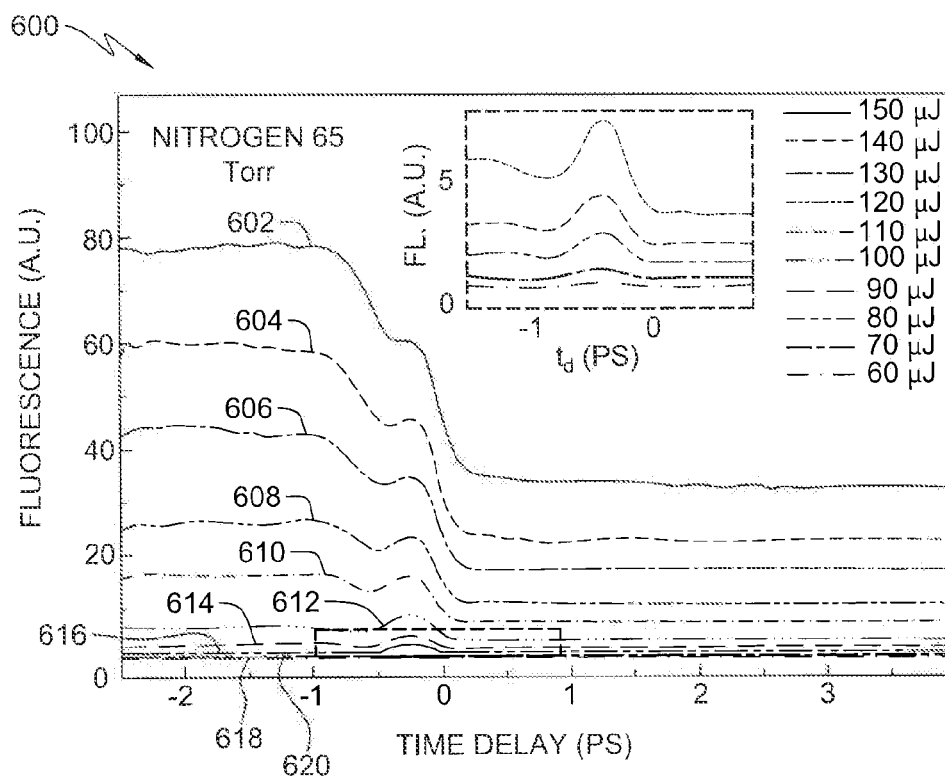
FIG. 6 is a graphical representation of fluorescence and relaxation time detected for nitrogen gas at varying laser-pulse excitation energies according to one aspect of the invention.
Figure 6:
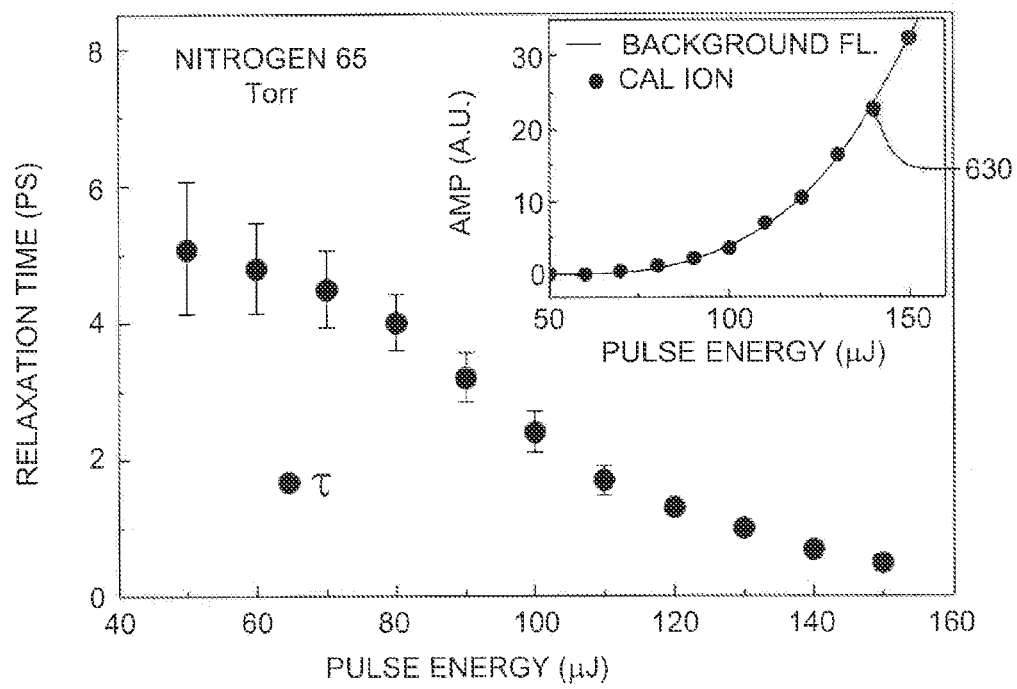

FIG. 6 is a graphical representation 600 of enhanced fluorescence and relaxation time detected for nitrogen gas at varying laser-pulse excitation energies, according to one aspect of the invention. FIG. 6 shows the electron collision dynamics under irradiation of laser pulses with different pulse energies. FIG. 6 first shows the measured change in fluorescence for different pulse energies with differing time delays. Curves 602-620 represent the fluorescence for a laser pulse with the specified intensity. The decrease of the average electron relaxation time with higher pulse energy is caused by the increased electron velocity and larger average scattering cross section due to the increased ion density. Curve 630 illustrates the pulse energy dependence on the measured background fluorescence signal and ion density using the ADK model.

Alternative gas mixtures under specific pressures of interest can be repeated using the steps described above. The plasma density and electron relaxation time can be determined, for example, for comparison to plasmas of unknown gases to identify those gases. Again referring to FIG. 1, terahertz radiation may be targeted at a plasma of an unspecified gas. The fluorescence or change in fluorescence can be observed and detected by a detector. The change in time-dependent fluorescence may be used to determine the plasma density, the electron relaxation time, or other characteristics of the unknown plasma. These characteristics may then be compared, for example, to the characteristics of known plasmas in order to determine the composition of the gas.

Optic beam or pulse 208 in FIG. 1 may be a single-color or a multi-color optic beam, for example, a laser beam having two or more frequencies, for example, frequencies ω and Ω, for example, frequencies of 800 nm and/or 400 nm. However, in one aspect, optic beam 208 may be a dual-color beam. For example, in one aspect, optic beam 208 may be dual-color. In one aspect, a dual-color beam may comprise a first frequency ω and a second frequency Ω may be a harmonic of first frequency ω, for example, about half first frequency ω. In one aspect, ω may be about 800 nm and Ω may be 400 nm (that is, twice the frequency but half the wavelength). Beam 208 may comprise pulses of multiple frequencies separated by a time delay, $t_D$, and have pulse energies ranging from 50 to 1000 microjoules [μJ], for example, between about 100 and 200 μJ, such as, 150 μJ.

In addition, in one aspect of the invention, by employing multi-color optical beams, for example, dual-color beam, to produce a plasma, spectroscopic information may also be encoded into the fluorescence emission 212 from plasma 100. For example, by using dual-color laser excitation to manipulate free electron drift, it is possible to modulate, for example, the fluorescence emission 212 or an acoustic emission (not shown) from a plasma whereby the plasma can be characterized. For example, the two-color aspect of the present invention may provide for coherent detection of a characteristic of a plasma, for instance, the detection of both an amplitude and a phase of a characteristic of a plasma.

It is believed that the application of this invention to the field of spectroscopy for use in any field of science and technology is very promising. It is conceived that multi-color optical beams may make it possible to obtain temporal characteristics of a plasma.

Contrary to the single-color aspects of the invention, in aspects of the invention employing two-color excitation, the synthesized optical field pulses generate ionized electrons with an asymmetric drift velocity. According to an aspect of the invention, the drift velocity distribution and electron trajectories can be regulated or controlled by the polarizations and relative phase of two optical fields, $\phi_{\omega,\Omega}$, for example, by varying the polarization and/or varying the relative phases of the two, or more, optical fields. After the passage of two-color pulses, for example, in pulse 208 in FIG. 2, the electric field of a single-cycle THz pulse 20 applied to the laser-induced plasma 100 alters the ionized electron momentum by acceleration or deceleration, depending on the electron initial velocity v. According to aspects of the invention, one or more characteristics of plasma 100 may be detected by at a different time delay $t_D$ between the THz pulse 210 and the optical pulse 208. According to aspects of the invention, one or more characteristic of plasma 100 may be determined by measuring time-dependent emission 212, for example, fluorescence emission or acoustic emissions, from plasma 100.

According to aspects of the invention, one or more characteristics of plasma 100, for example, time-dependent characteristics may be determined by determining the differential between the changes in an emission, for example, a change fluorescence $\Delta I_{FL}(t)$ for different optical fields $\Delta\phi_{\omega,\Omega}$, for example, for $\Delta\phi_{\omega,2\omega}$, or a change in acoustic emission. The florescence emission or the acoustic emission for any embodiment or aspect disclosed herein may be an enhanced emission, for example, an emission that varies, for instance, increases in amplitude, compared to a reference emission.

Thus, Terahertz wave enhanced fluorescence emission can be used to characterize a plasma. Time-dependent enhanced fluorescence may be correlated to plasma parameters, such as relaxation time and electron density. Plasmas may be characterized with a high temporal resolution and collected with omni-directional signal collection, which are essential for remote applications.

As will be appreciated by those skilled in the art, features, characteristics, and/or advantages of the various aspects described herein, may be applied and/or extended to any embodiment (for example applied and/or extended to any portion thereof).

Although several aspect of the invention have been described and depicted in detail herein, it will be apparent to those of skill in the art that various modifications, additions, substitutions, and the like can be made without departing from the spirit of the invention and these are therefore considered to be within the scope of the invention as defined in the following claims.

The invention claimed is:

1. A method of characterizing a plasma, comprising:
   directing THz radiation into the plasma; and
   detecting a time dependent THz wave enhanced fluorescence emission due to interaction of the THz radiation with the plasma to characterize the plasma.

2. The method as recited in claim 1, wherein the fluorescence emission is omnidirectional and detected in a direction divergent from a direction of propagation of the THz radiation.

3. The method as recited in claim 2, wherein detecting the fluorescence emission comprises detecting time dependent variation in the fluorescence emission.

4. The method of characterizing a plasma of claim 3, further comprising:
comparing the variation in fluorescence emission to a variation of fluorescence emission of known plasmas under the influence of the THz radiation.

5. The method of characterizing a plasma of claim 4, further comprising:
fitting the detected variation in fluorescence emission to a known equation to characterize the plasma.

6. The method as recited in claim 1, where the method further comprises:
determining a characteristic of the plasma by analyzing a time domain waveform of the detected THz wave enhanced fluorescence emission.

7. The method as recited in claim 6, where the characteristic of the plasma comprises at least one of plasma density, plasma scattering frequency, plasma relaxation time, and plasma electron density.

8. The method as recited in claim 6, wherein the method further comprises creating the plasma with a separate optic beam or pulse.

9. The method of characterizing a plasma of claim 8, wherein the separate optic beam or pulse comprises a multicolor optic beam or pulse, and said determining comprises coherent determination of a characteristic of the plasma.

10. The method of characterizing a plasma of claim 8, further comprising:
repeating the steps of creating the plasma, directing the THz radiation into the plasma and detecting the time dependent THz wave enhanced fluorescence emission with controlled variation in a time delay between the optic beam or pulse, and the THz radiation.

11. A plasma characterizing device comprising:
means for directing THz radiation into a plasma;
a detector detecting time dependent THz wave enhanced fluorescence emission emitted by the plasma due to interaction of the THz radiation with the plasma to characterize the plasma.

12. The plasma characterizing device of claim 11, further comprising:
means for directing a laser into a gas to create the plasma.

13. The plasma characterizing device of claim 12, wherein the THz radiation is a pulsed beam, and the laser has two or more frequencies.

14. The plasma characterizing device of claim 13, wherein the detector further comprises a filter.

15. The plasma characterizing device of claim 11, wherein the detector is not aligned with a direction of propagation of the THz radiation and comprises:
means for collecting the fluorescence emission; and
means for measuring the fluorescence emission.

16. A plasma characterizing system, comprising:
a gas cell, the gas cell having:
a gas inlet, configured to allow a gas to enter the gas cell;
a laser directing a laser beam or pulse at the gas within the gas cell, and exciting at least some of the gas to form a plasma;
a source of THz radiation directing the THz radiation into the plasma; and
a detector detecting time dependent THz wave enhanced fluorescence emission of the plasma.

17. The plasma characterizing device of claim 15, wherein a time delay between formation of the plasma by the laser beam or pulse and impact of the THz radiation on the plasma, is controllably varied.

18. The plasma characterizing device of claim 16, further comprising:
a collecting lens and at least one interference filter positioned between the plasma and the detector.

19. The plasma characterizing device of claim 16, wherein:
the THz radiation comprises a pulsed Terahertz wave, and the laser beam or pulse comprises a multi-frequency laser beam or pulse.

20. The plasma characterizing device of claim 16, wherein the detector is positioned angularly offset to a direction of propagation of the THz radiation.

* * * * *

UNITED STATES PATENT AND TRADEMARK OFFICE
CERTIFICATE OF CORRECTION

PATENT NO.         : 8,674,304 B2                                                Page 1 of 1
APPLICATION NO.    : 13/097866
DATED              : March 18, 2014
INVENTOR(S)        : Zhang et al.

It is certified that error appears in the above-identified patent and that said Letters Patent is hereby corrected as shown below:

In the Claims

Column 10, Line 25: Claim 17, Delete "claim 15" and insert -- claim 16 --

Signed and Sealed this
Nineteenth Day of August, 2014

Michelle K. Lee
*Deputy Director of the United States Patent and Trademark Office*